United States Patent [19]

White

[11] 4,128,954

[45] Dec. 12, 1978

[54] PACKAGE LABEL AND MANUFACTURE OF SAME

[75] Inventor: Rollin T. White, Westfield, N.J.

[73] Assignee: NJM, Inc., Hoboken, N.J.

[21] Appl. No.: 776,534

[22] Filed: Mar. 11, 1977

[51] Int. Cl.² ........................ G09F 3/00; A61F 13/02; B32B 3/14; B32B 7/06

[52] U.S. Cl. ........................................ 40/310; 40/594; 40/306; 40/312; 40/2 R; 283/19; 283/21; 206/459; 206/820; 428/40; 428/41; 428/42; 428/43; 428/77; 428/200; 428/201; 428/202; 428/211; 428/906

[58] Field of Search .................. 206/459, 820; 283/19, 283/21; 40/306, 310, 312, 125 A; 428/40, 41, 42, 43, 77, 200, 201, 202, 211, 347, 349, 352, 906

[56] References Cited

U.S. PATENT DOCUMENTS

| | | | |
|---|---|---|---|
| 3,484,976 | 12/1969 | Shea | 283/19 |
| 3,702,511 | 11/1972 | Miller | 283/21 |
| 3,854,229 | 12/1974 | Morgan | 428/40 |
| 3,924,744 | 12/1975 | Heimann | 206/820 |
| 3,993,814 | 11/1976 | Cavender | 428/40 |

*Primary Examiner*—William R. Dixon, Jr.

*Attorney, Agent, or Firm*—John J. Hart

[57] ABSTRACT

A printed product label is composed of at least two sections, at least one of which is provided with the label indicia pertinent to the product. One of the label sections is provided with an adhesive of one given type capable of affixing such label section permanently to the product. A second section is separably connected to the first section and is also provided with said given type of adhesive, but such adhesive thereon is employed to removably secure the second section to the product. The second section is additionally provided with a second adhesive of the pressure sensitive type that is masked to render it inoperative while the second label section is secured to the product, but which can readily be made operative when the second section is separated from the product and the first label section to adhere the separated second section to a backing member. The label may have additional label sections which may bear label indicia pertinent to the product and which are separably connected to the first and second sections, and which on their reverse sides may be blank, or provided with said given type of adhesive, or provided with masked adhesive of the pressure sensitive type.

7 Claims, 9 Drawing Figures

PACKAGE LABEL AND MANUFACTURE OF SAME

THE INVENTION

This invention relates to the manufacture of a novel form of label which is especially useful as a dispensing and recording label for medicinal and pharmaceutical products, although it can be employed advantageously on containers for other products.

In the marketing and dispensation of certain products, such as for example, medicinal preparations, it is necessary that the container for a particular product be properly labeled. The proper label for each such product should give certain information such as the name of the product, it's identifying code, and it's ingredients, the batch from which it was made, the net quantity in the container, the necessary caution relating to the dispensing and use of the product, and the name of the manufacturer or distributor. It is also desirable to construct the label so that it may be employed as a record of the sale of the product and/or the use of the product by a patient.

It is the primary purpose of this invention to provide a novel form of label capable of satisfactorily accomplishing all of the aforesaid functions.

For a better understanding of the invention reference is made to the accompanying drawings which show by way of example several ways of practicing the invention, and in which FIG. 1 is a face view of an unattached label embodying the invention that is especially suitable for use on a medicinal product;

Figure 4:
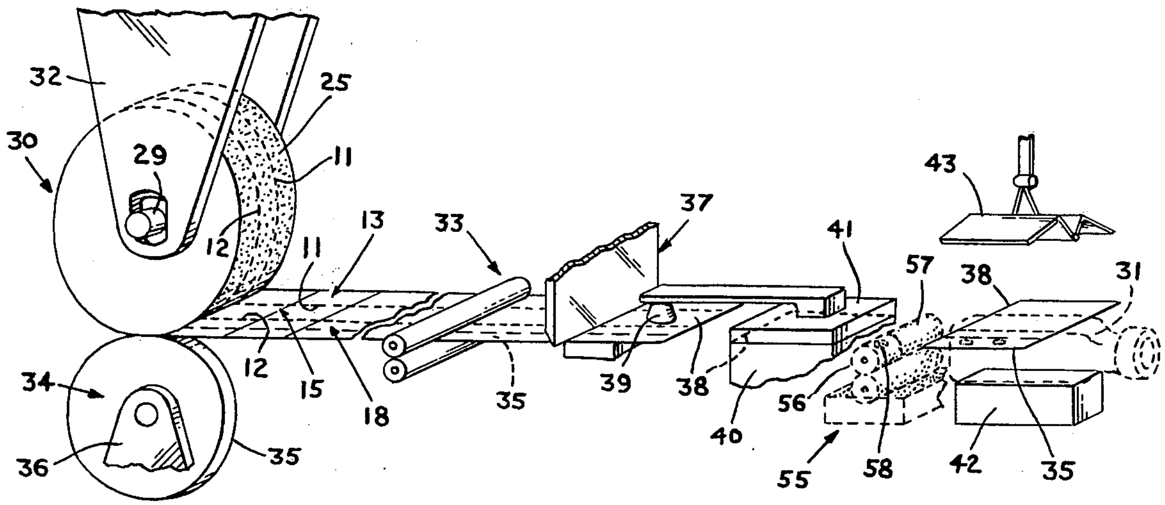
FIG. 4 is a perspective schematic view showing the means by which labels embodying the invention may be utilized in a labeling machine.

Reference is now made to FIGS. 1–4 of the drawings, which show by way of example a form of label embodying the invention that is preferred for labeling medicinal containers such as the four panel bottle 31 shown in FIG. 4 of the drawings. This label which is generally designated by the reference numeral 10, may be made of paper or other suitable flexible sheet material and is provided with two transverse lines 11 and 12 of perforations which divide the label into three readily separable sections, each of which will overlie one portion of a bottle such as the side panels of the bottle 31. The left side section 13 of the label, as viewed in FIG. 1 of the drawings, is provided with certain information 14, such as may be required by the pharmacist or other person who prepares the dosage for a particular patient. Thus, there may be printed on the face of side section 13, such information as the commercial name of the medicine, the date beyond which the medicine should not be used, the name of the active ingredient(s) in the medicine, the number of tablets or capsules in the container, the quantity of active ingredient(s) in each tablet or capsule, and the name and address of the manufacturer.

The middle section 15 of the label is provided with suitable label indicia 16 and may also include the information usually required by statute in labeling medicinal preparations. It may also be provided with information 17 capable of providing a record of the sale or disposition of the particular container to which the label has been applied.

The right side section 18 of the label, as shown, may be provided with the information 19 considered necessary for a complete record of the dosage taken by the patient. Thus, such information may include a notice as to the usual dosage, the commercial name of the medicine, the active ingredient(s) and the quantity thereof in each capsule or tablet, the number of capsules or tablets in the container, and the expiration date and lot number of the medicine. As shown, the label section 18 may also be provided with sufficient space 20 in which the doctor or nurse attending a patient may record the amount of the dosage for that patient and the time it is to be taken, or the frequency which it has been taken by such patient (note the right side section 18 shown in FIG. 5 of the drawings).

The reverse side of the label 10 is coated in its entirety with a suitable thermosensitive adhesive 25. The reverse side of the side section 18 of the label also has superposed on the thermosensitive adhesive 25 a strip 26 of a suitable pressure sensitive adhesive (compare FIGS. 2 and 3). While the adhesive strip 26 may be provided in any suitable manner on the back of the side section 18, it is preferred that it be located adjacently to the perforated line 12. The adhesive strip 26 is of sufficient width to enable the secure attachment of the side section 18 to a patient's chart, prescription or other record, as will hereinafter be more fully explained. The pressure sensitive adhesive strip 26 is properly masked by a strip or member 27 of suitable material capable of maintaining the pressure sensitive material active until it is needed for use and readily releasable from the latter when it is desired to effect the aforesaid attachment of the side section 18. A suitable material for this purpose is the known silicone treated paper liner or backing customarily used for this purpose.

Figure 2:
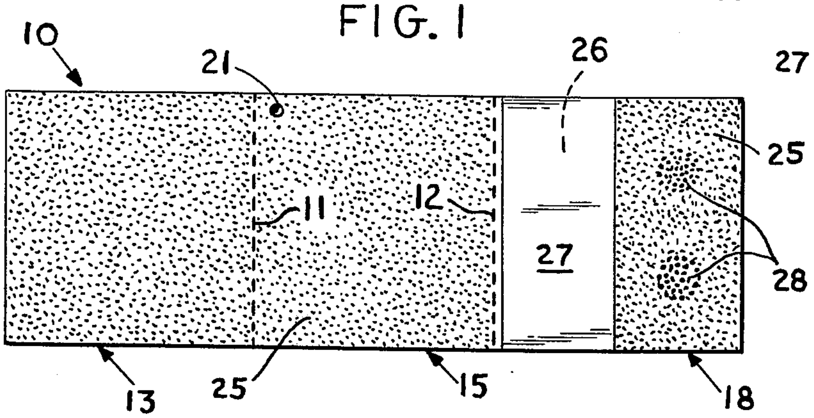
FIG. 2 is a view of the reverse side of the label shown in FIG. 1 and illustrates the manner in which different dual adhesives are provided on such reverse side.
Figure 3:
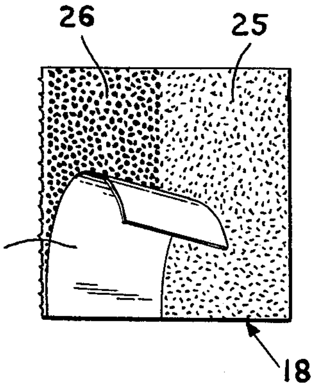
FIG. 3 is a view of the separated right side section of the label, as viewed in FIG. 2, and shows an adhesive masking strip being removed prior to attachment of such section by the masked adhesive to an article.
Figure 5:
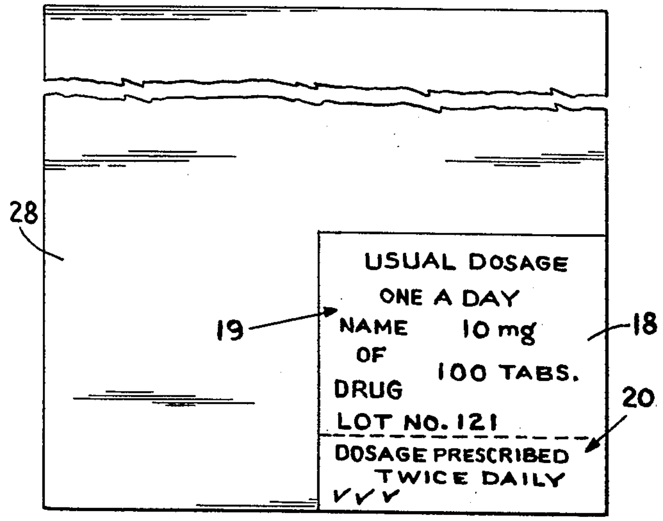
FIG. 5 is a face view of a patient's chart or record and showing the manner in which the right side label section shown in FIG. 3 may be attached thereto.

In applying the label 10 to a container the thermosensitive adhesive 25 on the reverse side of the label is acted upon by a heated pattern activator to adhesively activate the entire area of the portion of the thermosensitive adhesive 25 coating the left side label section 13 and one or two small areas of the portion of the thermosensitave adhesive 25 coating the right side label section 18; such small areas being indicated in FIG. 2 of the drawings by the dotted circles 28. Thus, the left side label section 13 will be completely and permanently adhered to the medicinal package, the center label section 15 will be completely unattached to the package since no heat was applied to the portion of the adhesive material 25 on this section, and the right side label section 18 will be only tacked to the package by the adhesively activated area portion(s) 28 of the thermosensitive adhesive material on such right side section. The pressure sensitive adhesive 26 on the label section 18 will be prevented from adhering to the package by the masking strip member 27. When the package is opened to dispense its contents, the center label section 15 and the right side label section 18 are readily torn off the container and separated from the left side label section 13 along the line of perforations 11. The center label section 15 can be readily separated from the right side label section 18 along the perforated line 12 and may be discarded, or kept as a record by the druggist or pharmacist. The label section 18 can then be attached to a prescription or patient's chart by the pressure sensitive adhesive 26 after the latter is exposed by the removal of the silicone treated strip of paper 27. When the label section 18 is stuck to a prescription or to a patient's chart 28 such as shown in FIG. 5 of the drawings, a nurse can readily ascertain from the printed matter 19 on such section and the instructions inserted by the doctor in the space 20 on such section, such information as the particular package from which the patient's medicine is to be obtained, the dosage, and the times such dosage is to be given to the patient. The nurse can also note in such space 20, such items as the number of times that she has given the medicine to the patient as indicated by the checks on the section 18 shown in FIG. 5 of the drawings. In this way there is readily available to the doctor a complete and accurate record of the treatment that has been accorded the patient.

An important feature of the above described label is that it can be made in roll form thereby avoiding the mixups that occur when loose, cut labels are used. The manufacturer is thus assured that the packages for a particular medicinal product will be labeled with the proper label for that product. The correctness of the applied label can be made a certainty by associating with each of, or a series of the labels in the roll, unique indicia, such as code bars or punched holes, discretely located with respect to the stated product and capable of being verified prior to or after the labels have been applied to the containers (note the punched hole 21 provided on the bottom edge portion of the label section 15). This label security is of utmost importance to manufacturers of medicinal and pharmaceutical products. By making the labels in roll form, they are also adaptable for use in existing high speed labeling machines. A roll of the type discussed is illustrated in FIG. 4 of the drawings, such roll being generally designated by the reference numeral 30. The roll is constituted of a continuous strip of paper provided on its face side with a series of labels similar to the previously described labels 10, and provided on its reverse side with a continuous coating 25 of unactivated thermosensitive adhesive. The label strip is wound so that the adhesive coating 25 is outermost. The roll 30 is supported in depending relation by a suitable U-shaped bracket 32 provided in the labeling machine. The roll 30 is mounted on a shaft 29 rotatably and removably mounted in vertical slots provided in the arms of the bracket 32 to enable the shaft 29 to shift to maintain the roll 30 in contact with an underlying roll 34 of pressure sensitive adhesive tape 35 as such rolls are depleted. The labels in the roll 30 are fed therefrom along a horizontal path in the labeling machine in any suitable manner, such as by the draw or register rolls 33 illustrated. The label web, as it is drawn from the roll, has its face side uppermost and its reverse adhesive coated side facing downwardly. At the place of discharge of the web from the roll, the adhesive coating 25 on the web is engaged by the roll 34 of pressure sensitive adhesive tape 35 which is supported by a U-shaped bracket 36 suitably mounted in the labeling machine. The pressure sensitive tape 35 is a known commercial product composed of a paper strip having the width of the aforesaid masking member 27 and treated with a release coating such as silicone so that both surfaces thereof have a release characteristic. The silicone treated strip is coated on its outer surface with a suitable pressure sensitive adhesive. The roll 34 is located with respect to the roll 30 so that as the label web is drawn from the latter, the adhesive tape 35 will be adhered to the adhesive coating 25 on the reverse side of the longitudinal portion of the label web from which are formed the right side label sections 18 and adjacent to the line of perforations 12 in the label web. It will be understood that when the adhesive tape 35 is so adhered to the adhesive coating 25, the grip of the pressure sensitive adhesive on the coating 25 will be greater than its adherence to the release treated surface of the adhesive coated strip. Thus, the latter may be readily stripped from the adhered pressure sensitive adhesive which remains on the adhesive coating 25.

Figure 9:
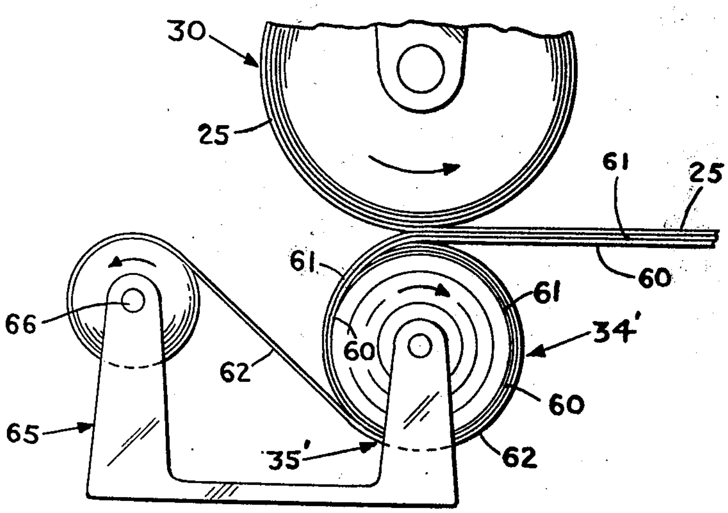
FIG. 9 is a partial front elevational view of the machine in FIG. 4 modified to use a pressure sensitive adhesive tape with two releasable treated strips.

It will be understood that other types of pressure sensitive adhesive tape may be employed instead of the type above discussed. For example, there is available on the market a pressure sensitive tape in which the pressure sensitive adhesive is sandwiched between two release treated strips. Thus, as shown in FIG. 9, the pressure sensitive adhesive tape 35' in the roll 34' is provided with a silicone treated strip 60 and a layer 61 of pressure sensitive adhesive comparable to the above described strip and adhesive, respectively, in the above described tape 35. In addition, the tape 35' has in engagement with the pressure sensitive adhesive 61 a second silicone treated strip 62. In mounting the strip 60 and adhesive 61 on the thermoplastic label adhesive coating 25 in the manner previously described with respect to the adhesive tape 35, the outer strip 62 is stripped from the adhesive 61 just prior to the engagement of the adhesive 62 with the label adhesive coating 25. To accomplish this the labeling machine is provided with means 65 for rotatably supporting a driven shaft 66 constructed to have releasably mounted thereon a roll core. The shaft 66 is rotated in a direction opposite to the direction of rotation of the roll 34' by any suitable means connected to the labeling machine drive in order to peel the outer silicone strip 62 from the tape 35' and wind it on the core provided on the shaft 66. When the roll 34' has been depleted, the roll formed from the wound strip 62 may be removed from the shaft 66 and replaced by a new core. The strip 60 and adhesive 61 which have been adhered to the label web will then be processed in the same fashion as the previously described tape 35.

Referring now to the showing of FIG. 4, in the operation of the labeling machine, as the combined label web and tape 35 are fed toward the label applying station, the leading labels 10 in the web may be periodically severed therefrom by suitable cutting mechanism 37. The severed leading or terminal label 38 may then be picked up by a vacuum device 39 of a known construction and delivered by the latter to a pickup station 40 where it is again picked up by a label applicator 41 and applied to the bottle 31 supported at the applying station 42. The vacuum device 39 and the applicator 41 may form part of a known dual pickup label carrier, as shown, so that as a label is being delivered by the device 38 to station 40, the applicator 41 is simultaneously delivering a previously deposited label from station 40 to the bottle 31. The applicator 41 is provided with a label carrying surface patterned similarly to the pattern in which the adhesive is to be activated on a label and is provided with a heating element for heating the patterned label carrying surface thereof so that as the applicator 41 transmits a label from station 40 to the bottle the thermosensitive adhesive 25 on the label is adhesively activated in the desired pattern. In depositing the label on the bottle the applicator 41 locates the label on the bottle so that the inner portion of the adhesive 25 on the left side label section 13 adjacent to the perforated line 11 is engaged with the top panel of the type of bottle 31 shown in FIG. 4 of the drawings. Because of the tackiness of the adhesive the label will remain in the position in which it is deposited by the applicator 41 on the bottle. Following the application of the severed label 38 to the bottle 31 it is secured to the bottle 31 by a hinged presser pad 43. In securing the label to the bottle, the two pivotal sections of the hinged presser pad 43 unfold to bend the label so as to adhere the label sections 13 and 18 to opposed panels of the bottle 31 and to cover the remainder of the top intermediate bottle panel with the unglued label section 15.

While in the practice illustrated in FIGS. 4 and 9, the tapes 35 and 35' are adhered to the label strip in the labeling machine, it will be understood that the label strip may have a pressure sensitive tape of the type of tape 35 adhered thereto before being made up into a roll such as the roll 30. Of course, in such case, there will be no need for the tape carrying bracket 36 in the labeling machine. Also, while FIG. 4 illustrates the use of a label roll in labeling articles, it will be understood, that instead of such roll, a stack of labels such as the label 10 illustrated in FIGS. 1 and 2 of the drawings may be utilized in the labeling machine and fed to the applying station 42 by a label applying drum equipped with suitable label transfer mechanism such as vacuum label applicators capable of removing the labels from the stack and applying them to bottles supplied to the applying station in a manner well known to the art.

Figure 1:
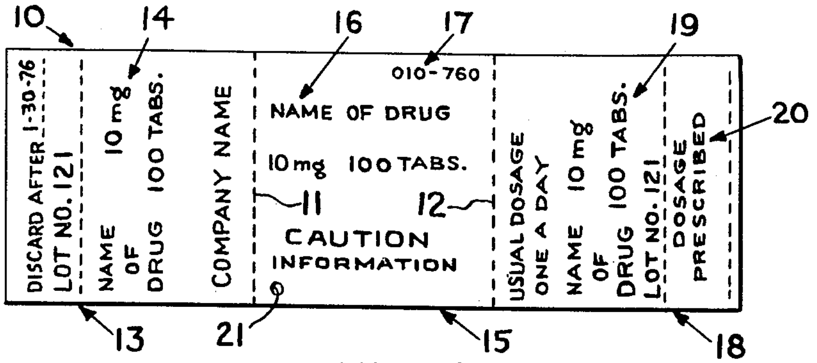
Figure 6:
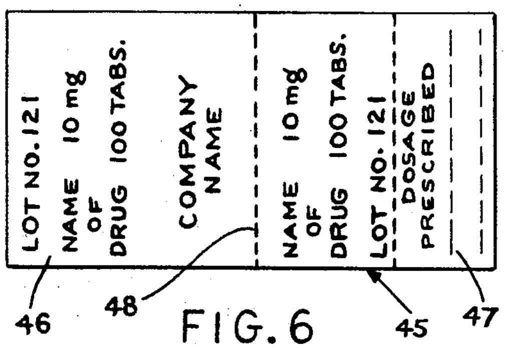
FIG. 6 is a face view of a modified form of label embodying the invention.
Figure 7:
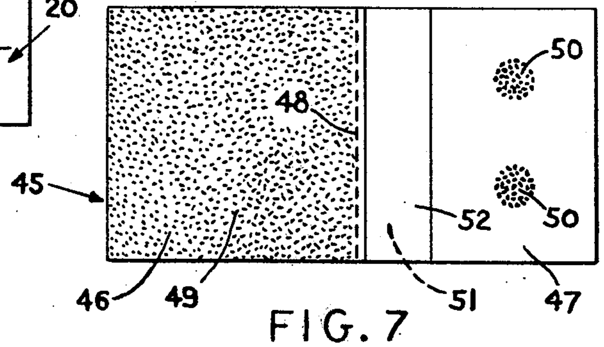
FIG. 7 is a reverse view of the label shown in FIG. 6.

Instead of being constructed of three parts or sections in the manner shown in FIGS. 1 and 2 of the drawings, the label of this invention may be made in two sections as is demonstrated by the label 45 shown in FIGS. 6 and 7 of the drawings. The label 45 is composed of a section 46 comparable to the previously described label section 13, but in addition to the information provided on the latter, there may also be printed on the label section 46 the information required by statute in labeling medicinal preparations. The other section 47 of the two section label, which is separated from the section 46 by a line of perforations 48, is comparable to the previously described label section 18. In addition to the information provided on the label section 18, the label section 47 may be provided with recording information such as the information 17 printed on the previously described label section 15. The reverse side of the two part label 45 may be entirely covered with a thermosensitive adhesive in the manner of the previously described three part label 10, or only partially covered with such adhesive. As is shown in FIG. 7 of the drawings, the reverse side of label 45 is provided with a coating 49 of thermosensitive adhesive which covers the entire area of section 46 of such label. The reverse side of section 47 of label 45 is provided with two areas 50 of thermosensitive adhesive which correspond to the heat activated areas 28 of the adhesive coating 25 on section 18 of the previously described three part label 10, and is otherwise free of such adhesive. It will be understood, that in practice the reverse side of the section 18 of the previously described three part label 10 may also be provided with only two areas of thermosensitive adhesive in the manner of the label section 47 herein described. Further, since the adhesive coating on the reverse side of the middle section 15 of the three part label 10 is not activated in the use of the label, such coating may be eliminated. With such changes in the adhesive coating of label 10, the thermosensitive adhesive coating on such label would correspond to the thermosensitive adhesive coating of label 45, as shown in FIG. 7. As with the previously described label section 18, the label section 47 is provided on its reverse side adjacent to the line of perforations 48, with a strip 51 of pressure sensitive adhesive that is masked by a strip of paper 52 treated by a releasing ingredient such as silicone to provide it with a readily detachable characteristic.

The use of the label 45 is similar to that described with respect to the label 10. The section 46 of label 45 will be permanently affixed to the medicine container and the section 47 will be releasably adhered to the container by the adhesive dots 50. The pressure sensitive adhesive 51 on label section 47 will not adhere to the container because of the treated strip 52. When the contents of the container are to be dispensed the label section 47 is readily separated from the label section 46 and the container and then attached to a prescription or patient's chart in the manner previously described with respect to the label section 18.

Figure 8:
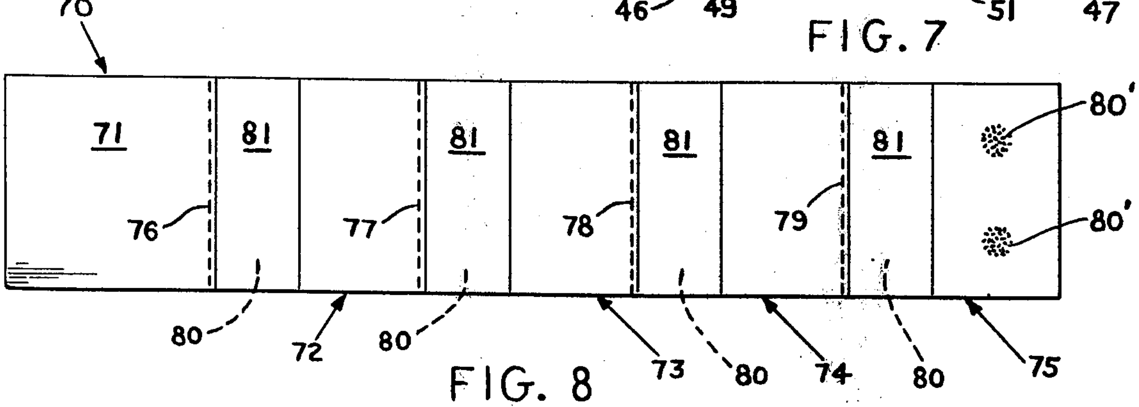
FIG. 8 is a plan view of the back of another form of label embodying the invention.

It is also contemplated that the label of this invention may be provided with more than three sections. Thus, the label, in addition to including a section such as illustrated by the sections 13 and 46 for permanent affixation to the product, may or may not include a section comparable to section 15, but may include a plurality of sections of the type of sections 18 and 47. A label of the indicated type without a section comparable to section 15 is illustrated in FIG. 8 of the drawings. In the label of FIG. 8, the left hand section 70, as viewed in such figure, is provided on its back with an adhesive 71 capable of affixing such label section 70 permanently to a product and in that respect is similar to the previously described sections 13 and 46. Also like sections 13 and 46, label section 70 is provided on its face with label indicia deemed desirable for such permanently affixed section. The label of FIG. 8 further includes four similarly constructed label sections 72, 73, 74 and 75 separably connected to each other and to the label section 70 by lines of perforations 76, 77, 78 and 79. Each of the label sections 72, 73, 74 and 75 is constructed along the lines of the previously described sections 18 and 47 and comprises on its face side the material previously indicated as suitable for the previously described sections 18 and 47 and on its back a strip 80 of pressure sensitive material masked by a release or silicone treated strip 81 of any suitable fabric such as paper. The back of at least one of the label sections 72, 73, 74 and 75 is also provided with an adhesive capable of removably securing it to the product in the manner of the adhesive materials 25 and 50 on the previously described label sections 18 and 47, respectively. In the label illustrated in FIG. 8 the terminal section 75 only is provided with such adhesive material 80'. It will be understood however, that one or more of the sections 72, 73 and 74 may also be provided with such adhesive material.

The use of the label shown in FIG. 8 is similar to that described with respect to the labels 10 and 45. However, the additional sections 72–75 provided with pressure sensitive material enables the recording material pertinent to such label to be made of record at a number of places where it is important that such record should be kept.

While in the above described label constructions, such labels, whether in roll or sheet form, have been provided with an unactivated glue on both the permanently and releasably attachable sections thereof prior to the introduction of such labels into the labeling machine, it will be understood that it is within the contemplation of this invention to provide the adhesive for permanently and releasably attaching the labels to the packages in the labeling machine. As is indicated in FIG. 4 of the drawings, this may be done by forming the roll 30 with a plain label web having no adhesive on its reverse side except the strip of pressure sensitive adhesive masked by the release treated paper strip. The adhesive for permanently and removably affixing the label sections to the product, whether thermoactivatable adhesive, ordinary label glue, or hot melt may be pattern coated on the severed label as it is being fed to the label applying station. The means for accomplishing this, as is indicated in dotted outline in FIG. 4 of the drawings, may be a suitable adhesive applying means 55 located between the pickup station 40 and the label applying station 42. As indicated, the adhesive applying means 55 may include a pattern roller 56 having a portion 57 for applying a coating of adhesive to the label section to be permanently attached to the package, and having portions 58 for applying small adhesive areas to the label section to be releasably connected to the package. The pattern roller 56 would apply the adhesive to the severed label 38 as it is being transported by the applicator 41 from the pickup station 40 to the bottle 31 to which it is to be applied.

It will be understood from the foregoing that the dual adhesive label of this invention whether made in two or more sections, is so constructed that it may be printed on either sheets or a continuous strip, thereby enabling it to be supplied to a product manufacturer in the form best suited for employment in the labeling machines of the manufacturer. As above indicated, roll labels are the type presently employed in the high speed labelers used by manufacturers in many industries because roll labels assure maximum label security and accountability, which factors are of great importance in certain of such industries. One of the sections on each label is permanently affixed to the container and is provided with full particulars as to the content of the containers. A second section of the label is separably connected to the first section and is merely adhesively tacked to the container so that it can readily be torn from both. The second section is also provided with an adhesive which is rendered inoperative to adhere such section to the container, but which can readily be made operative to adhere the separated section to a patient's prescription or record. The free side of the second section may contain information particularly of interest to a patient's doctor or druggist and may provide space enabling a record to be made of the dosages taken by the patient. If the label is provided with a third or additional sections, such as the middle section 14 of label 10 or the sections 72–75 of the label shown in FIG. 8, such sections can be utilized as records for purposes such as accountability of the particular container and its contents. It is contemplated that while such additional sections may or may not have provided thereon an adhesive similar to the adhesive on the first label section, they may be provided with a suitable masked pressure sensitive adhesive in the manner of the second section in the event the retailer or others desire to adhere such additional sections to backings or record sheets.

I claim:

1. The article which comprises a container for a product having a label bearing surface portion, and a label proper on such container comprising an unfolded sheet of label paper overlying said container surface portion as a single layer, said sheet being weakened transversely to provide two sections separable from one another, each of said sections having provided on its face side information relating to the particular product packaged in the container, a first of said sections having on its back side an adhesive permanently affixing said first section to the container, the second of said sections having on a first portion of its back side an adhesive removably affixing said second section to the container, whereby both of said sections hold the unfolded label sheet as a whole on the container in a form conforming to the shape of the container surface covered thereby, a pressure sensitive adhesive on a second portion of the back side of said second section and a second layer of material having a release coating thereon and covering said pressure sensitive adhesive to render the latter adhesively inoperative while said second label section is adhered to the container, said second layer being removable when said second label section is detached from the container and said first label section to render the pressure sensitive adhesive operative to adhere the back of the detached second label section to another article.

2. A label having a face side bearing label indicia and having a back side to be adhesively connected to a package but prior to such attachment being adhesively inoperative throughout its entire area, said label comprising a first layer having two sections separably connected together and each bearing on its face side indicia pertinent to a given product, the first of said sections having a back side adapted to be rendered adhesive to affix said first section permanently to a package, the second of said sections having on its back side in a reduced area thereof a pressure sensitive adhesive, the remainder of the back side area of said second section being adapted to be rendered adhesive to removably affix said second section to a package, whereby both sections of the applied label are capable of being simultaneously secured to the package to hold the label, as a whole, in a form conforming to the shape of the package surface covered by the label, the first section permanently and the other removably, a second layer of material having a release coating overlying the back side of said second section and covering only said pressure sensitive adhesive to render the latter adhesively inoperative when the back side of said second label section is adhesively secured to a package, said second layer being removable when said second label section is freed from its attachment to the package to render the reduced area of pressure sensitive adhesive operative to adhere the back of said freed second label section to another article.

3. A label as defined in claim 2, in which the back sides of both label sections are provided with inactive thermosensitive adhesive material, the thermosensitive material on the back of said first label section being capable of being adhesively activated to permanently affix said one label section to a package, and the thermosensitive material on the back of said second label section being capable of being adhesively activated to removably affix said second label section to a package, whereby when both sections are secured to a package said second label section may be detached from the package and said first label section without disturbing the attachment of said first label section to the package.

4. A continuous label strip composed of a longitudinally extending series of labels such as defined in claim 2 the labels being arranged in such strip that said pressure sensitive adhesive is disposed on the back of said label strip as a continuous longitudinal stripe located between the longitudinal side edges of said label strip, and said second layer of release coated material is in the form of a continuous strip extending longitudinally of the label strip and concealing said stripe of pressure sensitive adhesive.

5. A label having a face side bearing label indicia and having a back side provided with a non-pressure sensitive adhesive material to connect the label to a package, said label comprising two sections separably connected together and including a first section provided on its back side with an adhesive for affixing said first section permanently to the package, a layer of release treated material attached to the back side of the second of said sections and being in direct covering unattached engagement with the outer surface of the package when the label is affixed thereto, said layer of release treated material having a covering area less than the area of said second section, a coating of pressure sensitive adhesive attaching said layer of release treated material to the back side of said second section, and additional adhesive material on the back side of said second section in the area not covered by said layer of release treated material for removably securing said second section to the package, whereby both of said sections are secured to the package to hold the label, as a whole, in a form conforming to the shape of the package surface covered by the label until said second section is disengaged from the package for detachment from said first section, said layer of release treated material being removable from the detached second section to render the pressure sensitive adhesive on said second section operative to adhere said detached second section to another article.

6. A label as defined in claim 5, comprising a third section located between and separably connected to said first and second sections, said third section bearing on its face side indicia pertinent to said label indicia, the back of said third section being adhesively inoperative to enable said third section to cover an outer surface portion of the package in unattached condition when the label is applied to such package with said first and second sections secured thereto.

7. A label as defined in claim 5, comprising a third section separably connected to said first and second sections and bearing on its face side indicia pertinent to said label indicia, a second layer of release treated material attached to the back side of said third section and being in direct covering unattached engagement with the outer surface of the package when the label is affixed thereto, and a second coating of pressure sensitive adhesive attaching said second layer of release treated material to the back side of said third section, said second layer of release treated material being removable from said third section to render said second coating of pressure sensitive adhesive operative to adhere said third section, when separated from said first and second sections, to another article.

* * * * *